United States Patent
Colbaugh (10) Patent No.: US 9,707,409 B2
(45) Date of Patent: Jul. 18, 2017

(54) EFFICIENT CIRCADIAN AND RELATED SYSTEM MODULATION WITH A SLEEP MASK

(75) Inventor: Michael Edward Colbaugh, Level Green, PA (US)

(73) Assignee: Koninklijke Philips N.V., Eindhoven (NL)

(*) Notice: Subject to any disclaimer, the term of this patent is extended or adjusted under 35 U.S.C. 154(b) by 555 days.

(21) Appl. No.: 13/696,858

(22) PCT Filed: Apr. 25, 2011

(86) PCT No.: PCT/IB2011/051786
§ 371 (c)(1),
(2), (4) Date: Nov. 8, 2012

(87) PCT Pub. No.: WO2011/141840
PCT Pub. Date: Nov. 17, 2011

(65) Prior Publication Data
US 2013/0060306 A1   Mar. 7, 2013

Related U.S. Application Data (60) Provisional application No. 61/334,616, filed on May 14, 2010.

(51) Int. Cl.
*A61N 5/06* (2006.01)

(52) U.S. Cl.
CPC .... *A61N 5/0618* (2013.01); *A61N 2005/0628* (2013.01); *A61N 2005/0648* (2013.01); *A61N 2005/0652* (2013.01); *A61N 2005/0662* (2013.01)

(58) Field of Classification Search
CPC ........................................................ A61N 5/06
See application file for complete search history.

(56) References Cited

U.S. PATENT DOCUMENTS

| 4,858,609 | A | 8/1989 | Cole |
| 5,259,830 | A | 11/1993 | Masuda |
| 5,545,192 | A | 8/1996 | Czeisler et al. |
| 6,350,275 | B1 * | 2/2002 | Vreman et al. ............... 607/88 |
| 6,623,512 | B1 | 9/2003 | Heller et al. |
| 2005/0113891 | A1 * | 5/2005 | Pederson et al. ............ 607/88 |
| 2005/0159795 | A1 * | 7/2005 | Savage ................ A61M 21/00 607/88 |
| 2005/0237479 | A1 | 10/2005 | Rose |

(Continued)

FOREIGN PATENT DOCUMENTS

| AU | 2003203967 A1 | 11/2004 |
| JP | 02302276 A | 12/1990 |

(Continued)

OTHER PUBLICATIONS

M.J. Moseley; "Light Transmission Through the Human Eyelid: In Vivo Measurement", Dept. of Ophthalmology, vol. 8, Apr. 1998.

(Continued)

*Primary Examiner* — Lynsey Crandall (57) ABSTRACT

Light therapy is provided to a subject through a sleep mask. The sleep mask is configured to deliver electromagnetic radiation to the closed eyelids of the subject within a defined optimal wavelength band that is therapeutically impactful in modulating circadian and related systems of the subject.

12 Claims, 6 Drawing Sheets

(56) References Cited

U.S. PATENT DOCUMENTS

2006/0136018 A1 6/2006 Lack et al.
2011/0166631 A1* 7/2011 Breining .................. 607/88

FOREIGN PATENT DOCUMENTS

| JP | 0496764 A | 3/1992 |
|----|-----------|--------|
| JP | 2006525039 A | 11/2006 |
| JP | 2007061164 A | 3/2007 |
| WO | 2010076706 A1 | 7/2010 |
| WO | 2010076707 A1 | 7/2010 |
| WO | 2010076708 A1 | 7/2010 |
| WO | 2010076709 A1 | 7/2010 |

OTHER PUBLICATIONS

Ando et al; "Light Attenuation by the Human Eyelid", Society Biological Psychiatry, 1996, vol. 39, pp. 22-25.
Cole et al; "Bright-Light Mask Treatment of Delayed Sleep Phase Syndrome", Journal of Biological Rhythms, vol. 17, No. 1, Feb. 2002, pp. 89-101.
Hatonen et al; "Suppression of Melatonian by 2000-Lux Light in Humans With Closed Eyelids", Biol. Psychiatry, Sep. 15, 1999, vol. 46, No. 6, pp. 827-831.
Ando et al; "Light Mask 500 Lux Treatment for Delayed Sleep Phase Syndrome", Prog. Neuropsychopharmacol Biol Psychiatry, 1999, vol. 23, No. 1, pp. 15-24.
Rea et al; "A Model of Phototransduction by the Human Circadian System", Brain Research Reviews, vol. 50, 2005, pp. 213-228.
Van Den Pol et al; "Circadian System of Mice Integrates Brief Light Stimuli", Am. J. Physiol Regul. Integr. Comp. Physiol, vol. 275, No. 2, pp. 654-657. Aug. 1998.
Rimmer et al; "Dynamic Resetting of the Human Circadian Pacemaker by Intermittent Bright Light", Am. J. Physiol Regulatory Integratice Comp Physiol, vol. 279, pp. 1574-1579, 2000.
Ando et al, "Light Attenuation by the Human Eyelid", Biol. Psychiatry, vol. 39, 1996, pp. 22-25.
Hatonen et al, "Suppression of Melatonin by 2000-Lux Light in Humans With Closed Eyelids", Biol. Psychiatry, vol. 46, 1999, pp. 827-831.

* cited by examiner

Modeled Eyelid Transmittance vs. Wavelength (nm)

EFFICIENT CIRCADIAN AND RELATED SYSTEM MODULATION WITH A SLEEP MASK

The invention relates to the efficient modulation of circadian and related systems using optimized wavelength light therapy delivered through eyelids of a subject using a sleep mask.

The direction of radiation on a subject to impact the Circadian rhythms and/or to address disorders of the subject related to melatonin and/or serotonin levels in the subject are known. Generally, these treatments involve shining light directly towards a patient's eyes while the patient is awake to alleviate or cure light deficient disorders including Seasonal Affective Disorder (SAD), circadian sleep disorders and circadian disruptions associated with jet-lag, and shiftwork.

While some systems may be configured to administer phototherapy to a subject as the subject sleeps, these systems operate using light having less than optimal characteristics, which produces a less effective patient response, may expose patients to more light than necessary, and/or may utilize more power than necessary.

One aspect of the invention relates to a sleep mask configured to provide light therapy to a subject. In one embodiment, the sleep mask comprises a shield, a radiation source, and a controller. The shield is configured to cover the eyes of a subject wearing the sleep mask such that the shield provides a barrier between ambient radiation and the eyes of the subject. The radiation source is carried by the shield, and is configured to emit radiation onto the closed eyelid of the subject if the subject is wearing the sleep mask. The radiation emitted by the radiation source is within a wavelength band between about 490 nm and about 520 nm. The controller is configured to control emission of radiation by the radiation source according to a light therapy plan designed to impact a sleep cycle of the subject.

Another aspect of the invention relates to a method of providing light therapy to a subject. In one embodiment, the method comprises emitting electromagnetic radiation onto a closed eyelid of the subject, wherein the emitted radiation is within a wavelength band between about 490 nm and about 520 nm, and wherein the emitted radiation is emitted according to a light therapy plan designed to impact a sleep cycle of the subject.

Yet another aspect of the invention relates to a system configured to provide light therapy to a subject. In one embodiment, the system comprises means for emitting electromagnetic radiation onto a closed eyelid of the subject, wherein the emitted radiation is within a wavelength band between about 490 nm and about 520 nm, and wherein the emitted radiation is emitted according to a light therapy plan designed to impact a sleep cycle of the subject.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn in proportion to one another. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
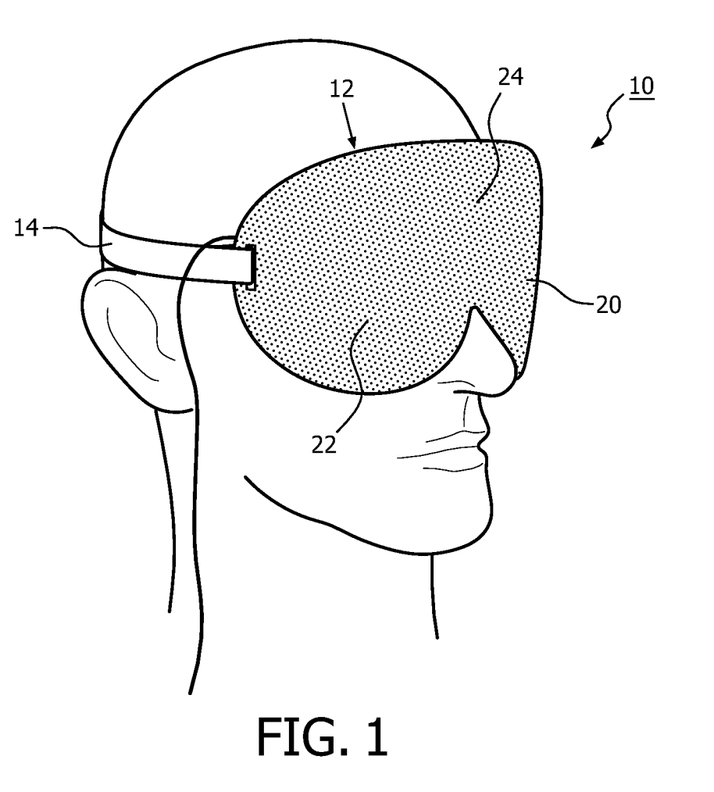
FIG. 1 illustrates a sleep mask, in accordance with one or more embodiments of the invention.
Figure 2:
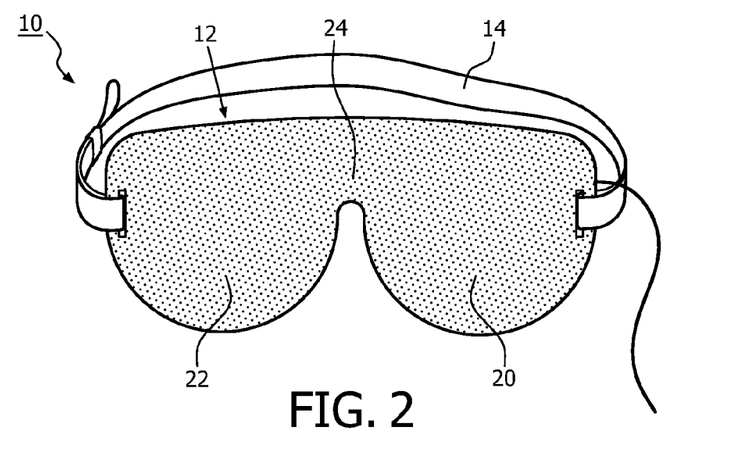
FIG. 2 illustrates a sleep mask, according to one or more embodiments of the invention.
Figure 3:
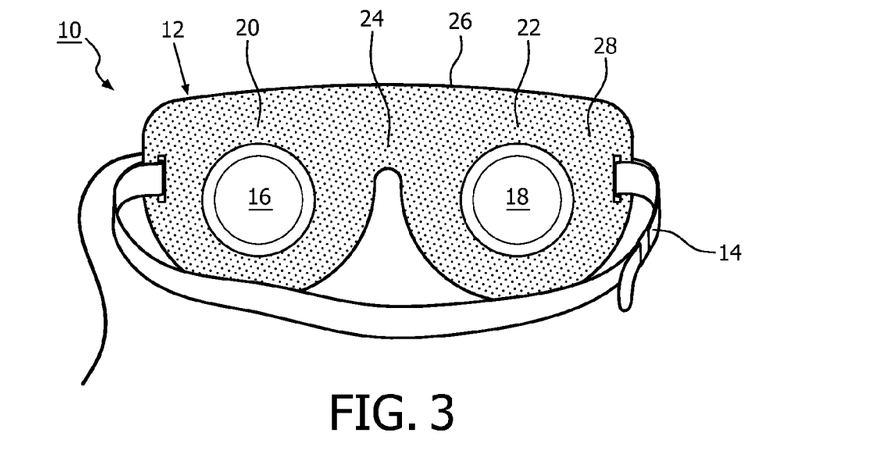
FIG. 3 illustrates a sleep mask, in accordance with one or more embodiments of the invention.

FIGS. 1-3 illustrate a sleep mask 10 configured to efficiently provide light therapy to a subject. The light therapy provided by mask 10 may be useful to modify circadian phases of the subject, modulate melatonin expression, and/or otherwise effect Retinal Ganglion Cell responses (e.g., seasonal affective disorder). The light therapy may include exposing the subject, through closed eyelids (e.g., during sleep time), to radiation having particular duration and patterns known to provide the aforementioned effects and/or other useful effects. Sleep mask 10 described herein provides this therapy more efficiently, by using radiation within and optimized wavelength band that enables optimized light exposure, power consumption and efficacy.

Sleep mask 10 may provide a comfortable delivery mechanism for the light therapy, and may deliver the light therapy to the subject while the subject is asleep, in the process of going to sleep, and/or waking from sleep. In one embodiment, sleep mask 10 includes one or more of a shield 12, a strap 14, a first lighting module 16, and/or a second lighting module 18.

As can be seen in FIG. 1, shield 12 is configured to cover the eyes of the subject wearing sleep mask 10. In one embodiment, shield 12 includes a first shield portion 20 and a second shield portion 22. First shield portion 20 is configured to cover a first eye of the subject. Second shield portion 22 is configured to cover a second eye of the subject. In order to comfortably cover the first eye and the second eye of the subject, first shield portion 20 and second shield portion 22 are substantially larger than the ocular openings of the eyes of the subject.

In one embodiment, first shield portion 20 and second shield portion 22 are joined by a connecting shield portion 24. Connecting shield portion 24 is configured to rest on at least a portion of the nose of the subject (e.g., across the bridge of the nose) when the subject is wearing sleep mask 10. In some instances (not shown), connecting shield portion 24 may be narrower or thicker than the embodiment depicted in FIGS. 1-3.

In one embodiment, shield 12 is formed from flexible materials. The flexibility of shield 12 may enhance the comfort of shield 12 to the subject. The side of shield 12 visible in FIG. 3 faces toward the subject during use. On this side, a base surface 26 substantially impermeable to liquids may be formed. For example, the impermeable base surface 26 may be formed by a flexible plastic material such as polycarbonate, polyester, and/or other materials. The impermeability of base surface 26 may protect electronic components of sleep mask 10 carried within shield 12 from moisture.

In one embodiment, shield 12 includes a cushioning layer 28 disposed on base surface 26. Cushioning layer 28 is formed from a soft, resilient material. For example, cushioning layer 28 may be formed from foam, fabric, fabric/foam laminate, and/or other materials. During use, cushioning layer 28 provides the innermost surface to the subject, and engages the face of the subject. As such, the softness of cushioning layer 28 provides a cushion for the face of the subject, and enhances the comfort of sleep mask 10 to the subject.

As will be appreciated from the foregoing and FIGS. 1-3, during use shield 12 provides a barrier between ambient radiation and the eyes of the subject. In one embodiment, shield 12 is opaque, and blocks ambient radiation (at least within the visible spectrum), thereby shielding the eyes of the subject from ambient radiation.

Strap 14 is configured to hold shield 12 in place on the subject. In the embodiments shown in FIGS. 1-3, strap 14 is attached to each of first shield portion 20 and second shield portion 22, and wraps around the head of the subject to hold sleep mask 10 in place on the head of the subject. Strap 14 may be adjustable in length (e.g., to accommodate different sized heads). Strap 14 may be formed from a resilient material (e.g., elastic) that stretches to accommodate the head of the user and holds shield 12 in place. It should be appreciated that the inclusion of strap 14 in the embodiments of sleep mask 10 illustrated in FIGS. 1-3 is not intended to be limiting. Other mechanisms for holding shield 12 in place on the subject are contemplated. For example, a more elaborate headgear may be implemented, an adhesive surface may be applied to shield 12 that removably adheres to the skin of the subject to hold shield 12 in place, a rigid or flexible frame (e.g., eyeglasses), and/or other mechanisms for holding shield 12 in place may be implemented.

Referring now to FIG. 3, first lighting module 16 and second lighting module 18 are mounted to first shield portion 20 and second shield portion 22, respectively, on the side of shield 12 that faces toward the face of the subject during use. First lighting module 16 and second lighting module 18 are backlit, and are configured to emit radiation onto the face of the subject on and/or about the eyes of the subject. As is discussed below, the radiation emitted by first lighting module 16 and second lighting module 18 has a wavelength (or wavelengths) that have a therapeutic impact on the subject, when they are delivered in accordance with an effective light therapy plan.

The target of the light therapy plan are the intrinsically photosensitive Retinal Ganglion Cells. The intrinsically photosensitive Retinal Ganglion Cells are a type of nerve cell in the retina that do not participate directly in vision. Instead, the intrinsically photosensitive Retinal Ganglion Cells are non-image-forming, and provide a stable representation of ambient light intensity. As a result, the intrinsically photosensitive Retinal Ganglion Cells participate in at least three key areas: (1) they play a role in synchronizing circadian rhythms to the light/dark cycle by providing length of day, length of night, and night-to-day and day-to-night transitional information, (2) the contribute to the regulation of pupil size, and (3) they contribute to photic regulation of, and acute photic suppression of, release of the hormone melatonin. For convenience, within this disclosure, the term "sleep cycle" will be used to refer to the circadian rhythms, and/or the production, suppression, and/or release of melatonin for the subject. Given the information above, light therapy can be used to modify circadian phases of the subject, modulate melatonin expression, and/or otherwise effect Retinal Ganglion Cell responses or visual system-related body function (e.g., treat pathologies such as seasonal affective disorder) through various brain centers, including: thalamus, SCN (suprachiasmatic nucleus), IGL (intergeniculate leaflet), hypothalamus, and other bodily centers.

Figure 4:
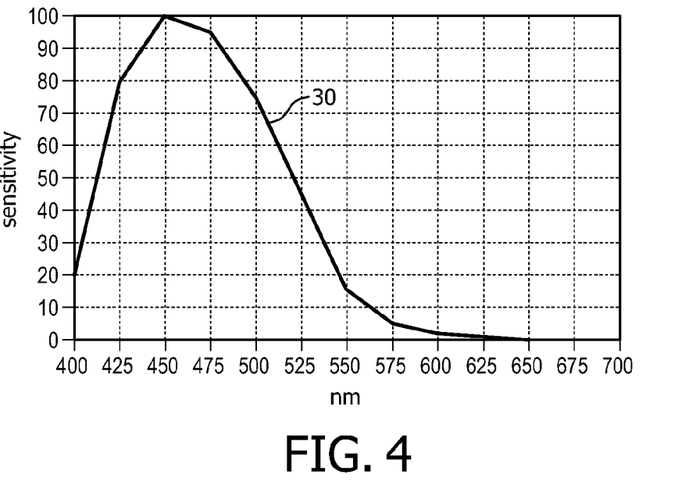
FIG. 4 illustrates a plot showing the response of intrinsically photosensitive Retinal Ganglion Cells versus wavelength.

FIG. 4 provides a plot 30 showing the response of intrinsically photosensitive Retinal Ganglion Cells versus wavelength. As can be seen in FIG. 4, the sensitivity of the intrinsically photosensitive Retinal Ganglion Cells peaks at approximately 450 nm, and drops off dramatically to an inflection point at approximately 550 nm. By virtue of this sensitivity profile, conventional light therapy systems and plans have focused on providing electromagnetic radiation to the eye of the subject between 450 nm and 475 nm. Particularly light therapy systems and plans in which electromagnetic radiation is provided directly to the open eye of the subject. In many instances, however, it is desirable to provide light therapy to a patient during sleep. As such, radiation must be delivered through a subject's eyelids, which necessarily attenuates any delivered radiation to a certain degree.

Figure 5:
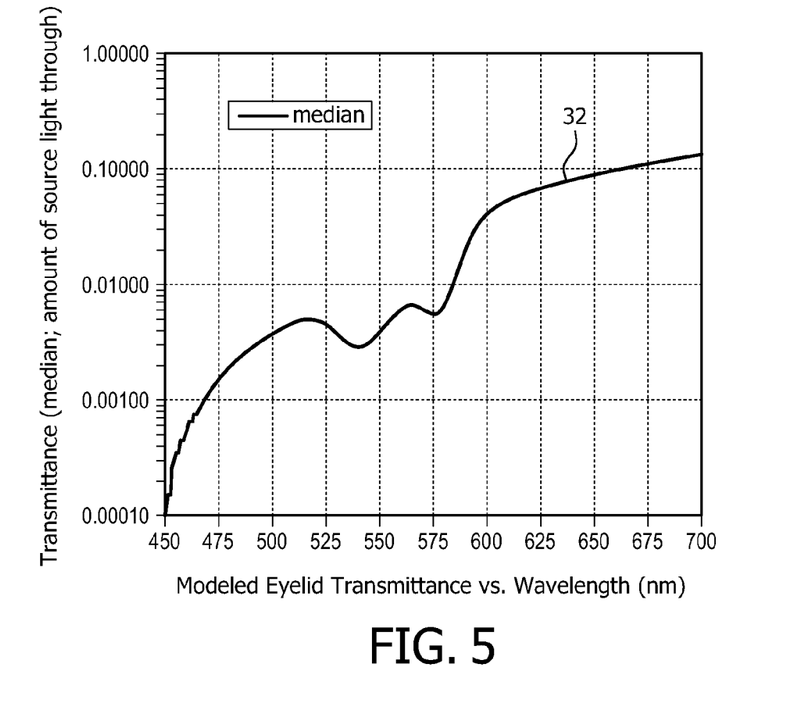
FIG. 5 illustrates a plot of transmittance of the human eye lid (on a logarithmic scale) versus wavelength.

FIG. 5 provides a plot 32 of transmittance of the human eye lid (on a logarithmic scale) versus wavelength. As can be seen in FIG. 5, transmittance through the eyelid varies somewhat dramatically based on wavelength. As such, although electromagnetic radiation at 450 nm may be the most efficient radiation for impacting intrinsically photosensitive Retinal Ganglion Cells to shift the sleep cycle when directing electromagnetic radiation to an open eye, attenuation of electromagnetic radiation at 450 nm may reduce the efficiency of this wavelength when electromagnetic radiation is being provided to the eye of the subject through the eyelid (e.g., as is done by the sleep mask 10 shown in FIGS. 1-3). FIG. 5 illustrates that circadian modifying light in the range of about 450-550 nm is attenuated by a factor of ten (10) or greater than longer wavelength light (e.g. wavelengths greater than 575 nm) as light passes through the eyelids. Within this band, as the curve moves towards the "blue" end of the spectrum (i.e., towards 450 nm) attenuation increases. As such, radiation within the range useful for light therapy towards the green-blue end of the spectrum will be less attenuated by a patient's eyelid.

Figure 6A:
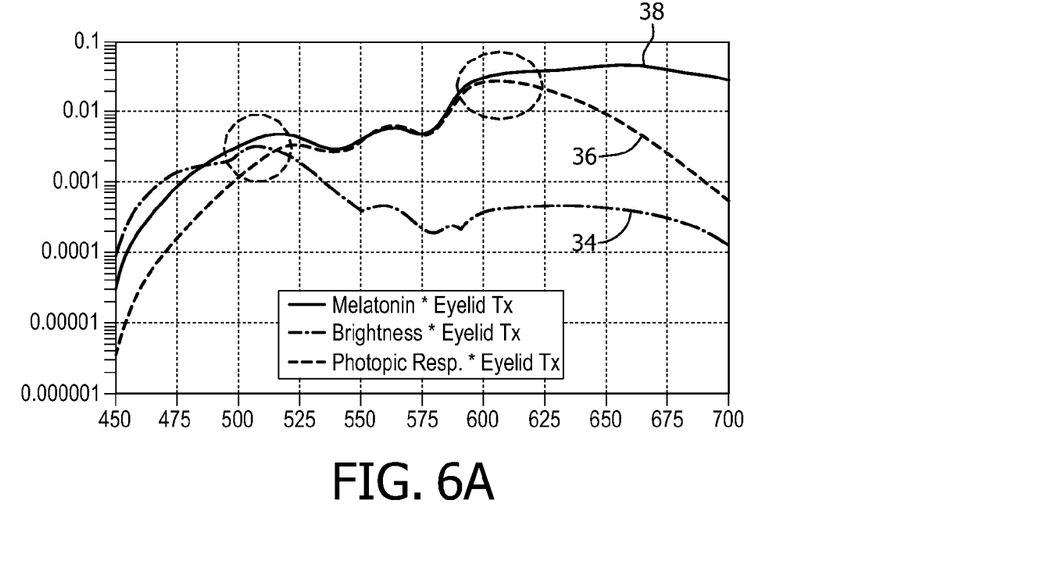
FIG. 6A illustrates a plot of sleep cycle sensitivity, a plot of photopic response, and a plot of relative sensitivity of the visual system for electromagnetic radiation that has passed through the eyelid of the subject.

FIG. 6A provides a plot of sleep cycle sensitivity 34, a plot of photopic response 36, and a plot of relative sensitivity of the visual system 38 for electromagnetic radiation that has passed through the eyelid of the subject. In other words, plots 34, 36, and 38 have been adjusted for the transmittance of the human eye lid (e.g., as shown in plot 32 of FIG. 5, discussed above). As can be seen in FIG. 6A, the transmittance of the human eyelid shifts the optimal wavelength for impacting the sleep cycle of the subject through light therapy from around 450 nm to between about 490 nm and about 520 nm or between about 500 nm and about 510 nm.

Figure 6B:
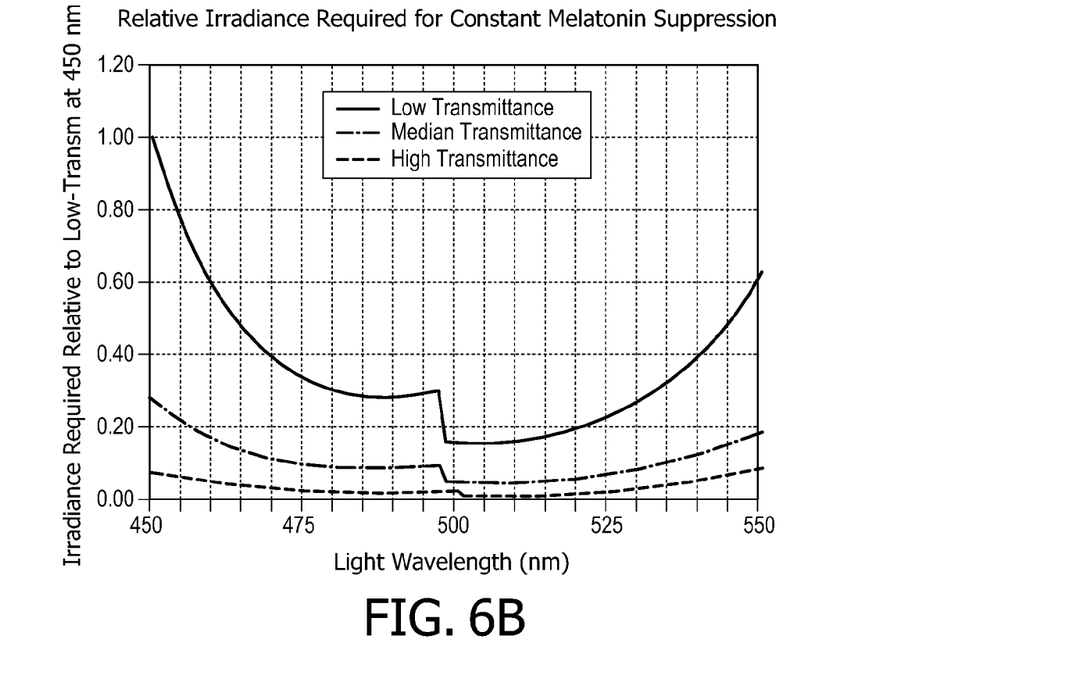
FIG. 6B illustrates plots of relative irradiance of light wavelengths projected through the eyelids of subjects required for constant melatonin suppression.

Furthermore, FIG. 6B illustrates the relationship of irradiance (i.e., radiant power) to wavelength of light required for constant melatonin suppression in subjects. FIG. 6B illustrates a low transmittance curve 35 representing persons whose eyelids have low transmittance of light, a median transmittance curve 37 representing the median values of eyelid transmittance of light, and a high transmittance curve 39 representing persons having a high transmittance of light. As can bee seen by the data in FIG. 6B, the median light transmittance (curve 37) in the 500 nm to 510 nm band is approximately $1/300^{th}$ of the incident light on the outside of the eyelids. The collected transmittance data also demonstrates that there is approximately a 10:1 range on the characteristic over the population (the difference in the "high transmittance" and the "low transmittance" curves). As past data was based on small numbers of subjects and/or a limited number of monochrome wavelengths, this difference was missed and not accounted for in prior light therapy treatments. The highest eyelid attenuation that was measured recently allowed only $1/1000^{th}$ of the incident light in the optimum band of 500 nm to 510 nm to pass. The lowest attenuation value allowed approximately $1/100^{th}$ of the incident light in the 500 nm to 510 nm band to pass. However, all subjects had approximately the same transmittance curve shape (i.e., the same local minima/minima locations across the spectrum), as is seen in FIG. 6B. Thus, it is clear that the light in the range of about 490 nm to about 520 nm or about 500 nm to about 510 nm is provides optimal transmittance through patient eyelids (regardless of differences in subject transmittance) within the wavelength band useful for light therapy. As such, in some embodiments, the light used by sleep mask 10 does not have substantial power in wavelengths shorter than about 490 nm or greater than about 520 nm, or shorter than about 500 nm or greater than about 510 nm, for the purpose of stimulating circadian systems related to photo response.

In contrast with the widely used 440 nm to 480 nm ("blue") wavelengths for opened eyes, the optimal "green-blue" wavelength band for closed eyes (i.e., 490 nm-520 nm) is also an order of magnitude safer with respect to causing short wavelength damage to a subject's visual receptors. As such, light intensity used when providing closed eye light therapy in the optimized range can be 10 to 1000 times the intensity levels for open eye treatment.

As such, the data discussed above enable optimization of the wavelength used for closed eye light therapy informs that lower levels of light are needed for melatonin suppression (and thus, circadian and related sleep cycle system modulation) when radiation in the 490 nm to 520 nm range or the 500 nm to 510 nm range is used. Therefore, less radiation has to be generated outside the eyelid and directed onto the eyelid to obtain a given effect. Accordingly, if more effect is desired, more radiation may be used, if desired or necessary. Again, light intensity used when providing closed eye light therapy in the optimized range can be 10 to 1000 times the intensity levels for open eye treatment. Thus, use of this optimized wavelength band provide more efficient light therapy. This efficiency realization enables light therapy to be optimized, not only for efficacy, but for patient light exposure, light mask power consumption, and may provide other benefits.

Referring back to FIG. 3, in one embodiment, to enhance the efficiency of the light therapy provided to the subject, first lighting module 16 and second lighting module 18 are configured to emit electromagnetic radiation in a first wavelength band that is shifted to account for attenuation by the eyelid of the subject. For example, the first wavelength band may include wavelengths between about 490 nm to about 520 nm and/or between about 500 nm to about 510 nm.

Figure 7:
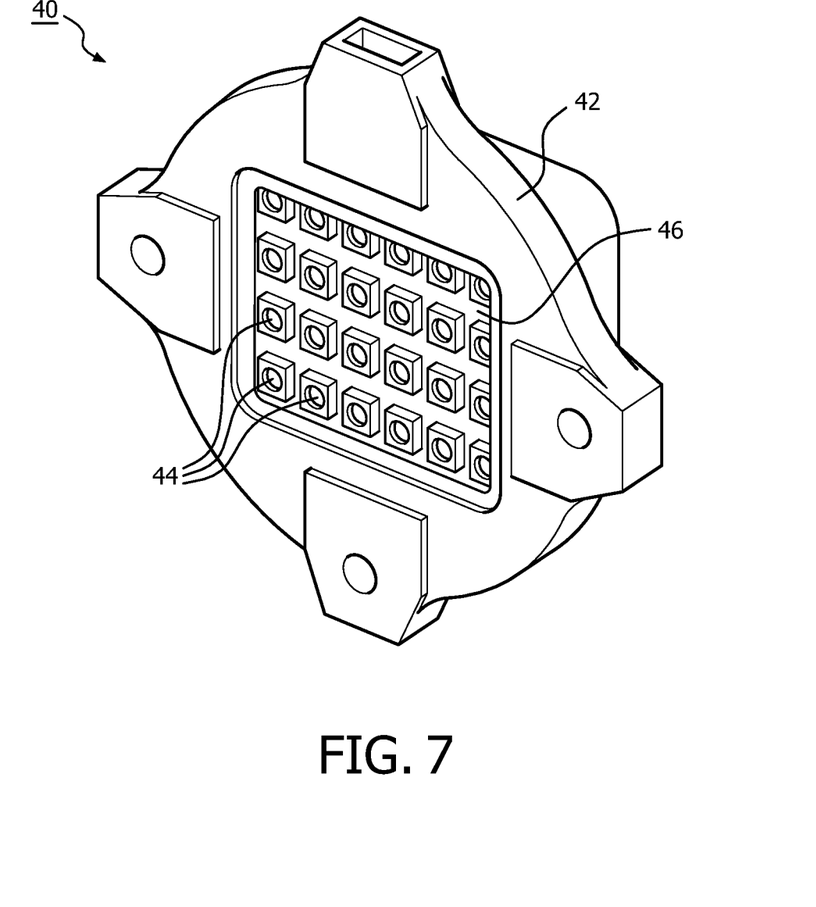
FIG. 7 illustrates a lighting module, in accordance with one or more embodiments of the invention.

FIG. 7 illustrates a lighting module 40. The lighting module 40 may be implemented in a sleep mask similar to or the same as sleep mask 10 (shown in FIGS. 1-3), and may serve as a first lighting module similar to or the same as first lighting module 16 and/or a second lighting module similar to or the same as second lighting module 18 (shown in FIGS. 1-3). The lighting module 40 may include one or more of a housing 42, one or more radiation sources 44, and/or other components.

The housing 42 is configured to house and/or carry one or more radiation sources 44. The housing 42 is attachable (permanently or temporarily) to a sleep mask for use by the subject. As such, housing 42 may be formed from a rigid material, or housing 42 may be formed from a material with some resilient elasticity in order to provide comfort to the subject. As can be seen in FIG. 7, in one embodiment, housing 42 is configured to seat a substrate 46 carrying radiation sources 44. Housing 42 may further be configured to carry an optical diffuser on the outside of radiation sources 44. This will help to diffuse the electromagnetic radiation emitted by radiation sources 44, and provide electromagnetic radiation having a substantially uniform distribution onto the eyelid of the subject. This may enhance the comfort and/or usability of lighting module 40 during rest and/or sleep by the subject.

As discussed herein, in some embodiments, radiation sources 44 may be configured to emit electromagnetic radiation in a band of wavelengths between 500 nm and 510 nm. Radiation sources 44 may be arranged in lighting module 40 such that if when lighting module 40 is installed in a sleep mask, the electromagnetic radiation emitted by radiation sources 44 is directed onto the eyelid of the subject. Some of the electromagnetic radiation then passes through the eyelid and into the eye of the subject, where it impinges on the intrinsically photosensitive Retinal Ganglion Cells of the subject, and has a therapeutic impact on the sleep cycle of the subject (e.g., shifting the sleep cycle, prolonging the sleep period, etc.).

Figure 8:
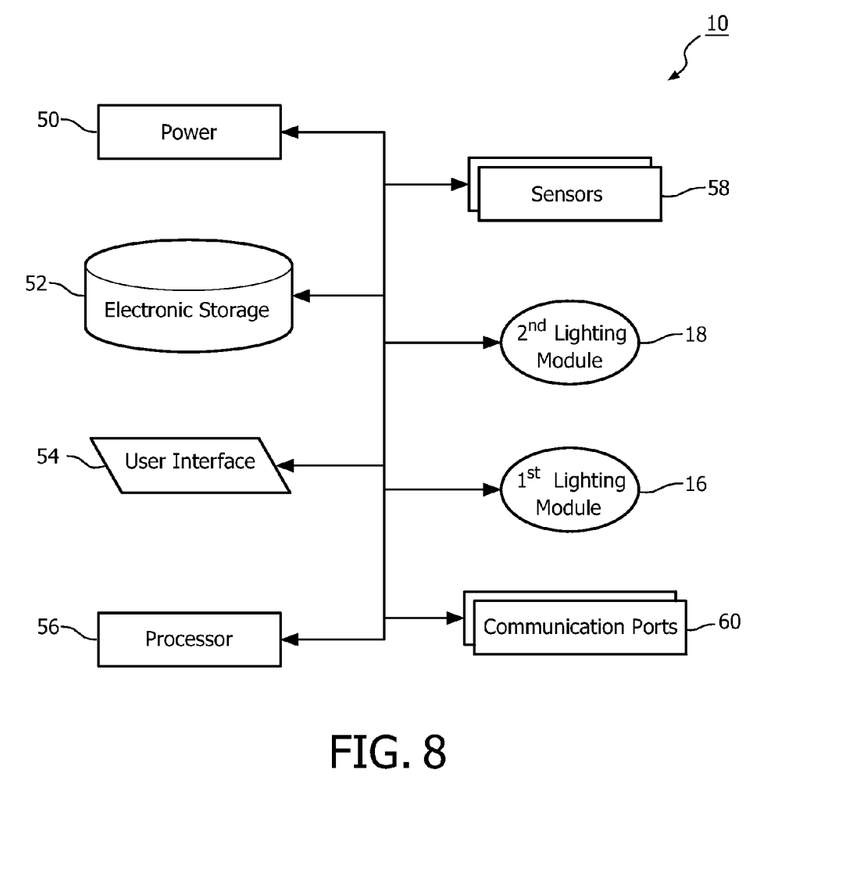
FIG. 8 illustrates a schematic diagram of a sleep mask, in accordance with one or more embodiments of the invention.

FIG. 8 is a schematic illustration of sleep mask 10, in accordance with one or more embodiments of the invention. As can be seen in FIG. 8, in addition to one or more of the components shown in FIGS. 1-3 and described above, sleep mask 10 may include one or both of a power source 50, electronic storage 52, a user interface 54, a controller 56, one or more sensors 58, and/or one or more communication ports 60. In one embodiment, one or more of power source 50, user interface 54, controller 56, sensors 58, and/or communication ports 60 are carried on shield 12 and/or strap 14 of sleep mask 10. In this embodiment, one or more of power source 50, electronic storage 52, user interface 54, controller 56 sensors 58, and/or communication ports 60 may be removably attached to shield 12 and/or strap 14, and may be disconnectable from the rest of sleep mask 10. This will enable power source 50, electronic storage 52, user interface 54, controller 56, sensors 58, and/or communication ports 60 to be removed from a given shield 12 and/or strap 14, and attached to another shield 12 and/or strap 14, which may be beneficial if shield 12 and/or strap 14 degrade over time and/or with usage and must be replaced. Similarly, in one embodiment, first lighting module 16 and second lighting module 18 are also removable/replaceable on shield 12. Power source 50, electronic storage 52, user interface 54, and/or controller 56 may control operation the radiation sources associated with first lighting module 16 and/or second lighting module 18, as is discussed below.

Power source 50 provides the power necessary to operate the radiation sources associated with first lighting module 16 and second lighting module 18, and/or to power electronic storage 52, user interface 54, and/or controller 56. Power source 42 may include a portable source of power (e.g., a battery, a fuel cell, etc.), and/or a non-portable source of power (e.g., a wall socket, a large generator, etc.). In one embodiment, power source 50 includes a portable power source that is rechargeable. In one embodiment, power source 50 includes both a portable and non-portable source of power, and the subject is able to select which source of power should be used to provide power to sleep mask 10.

In one embodiment, electronic storage 52 comprises electronic storage media that electronically stores information. The electronically storage media of electronic storage 52 may include one or both of system storage that is provided integrally (i.e., substantially non-removable) with sleep mask 10 and/or removable storage that is removably connectable to sleep mask 10 via, for example, a port (e.g., e.g., a communication port 60 such as, for example, a USB port, a firewire port, etc.) or a drive (e.g., a disk drive, etc.). Electronic storage 44 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 52 may store software algorithms, information determined by controller 56, information received via user interface 54, and/or other information that enables sleep mask 10 to function properly. Electronic storage 52 may include media provided as a separate component within sleep mask 10. Electronic storage 52 may include media provided integrally with one or more other components of sleep mask 10 (e.g., controller 56).

User interface 54 is configured to provide an interface between sleep mask 10 and the subject (and/or a caregiver) through which the subject (and/or a caregiver) may provide information to and receive information from sleep mask 10. This enables data, results, and/or instructions and any other communicable items, collectively referred to as "information," to be communicated between the subject and controller 56. Examples of interface devices suitable for inclusion in user interface 54 include a keypad, buttons, switches, a keyboard, knobs, levers, a display screen, a touch screen, speakers, a microphone, an indicator light, an audible alarm, and a printer. In one embodiment, the functionality of which is discussed further herein, user interface 54 actually includes a plurality of separate interfaces, including one interface that is carried on sleep mask 10, and a separate interface provided to view and/or manage stored information that has been retrieved from sleep mask 10 (e.g., provided by a host computer to which information from sleep mask 10 can be received).

It is to be understood that other communication techniques, either hard-wired or wireless, may also be provided by one or more communication ports 60. For example, the present invention contemplates that mask 10 may be integrated with a removable storage interface provided by electronic storage 52. In this example, information may be loaded into sleep mask 10 from removable storage (e.g., a smart card, a flash drive, a removable disk, etc.) that enables the user(s) to customize the implementation of sleep mask 10. Other exemplary input devices and techniques adapted for use with sleep mask 10 include, but are not limited to, an RS-232 port, RF link, an IR link, modem (telephone, cable or other). In short, any technique for communicating information with sleep mask 10 is contemplated by the present invention. One or more communication ports 60 may also be used to communicate with additional devices or computing machines for the purposes of programming controller 56, retrieving data from storage 52, adding functionality to mask 10 (e.g., by way of interfacing with additional equipment), and/or for other purposes.

Controller 56 is configured to provide information processing and/or system control capabilities in sleep mask 10. As such, controller 56 may include one or more of a digital processor, an analog processor, a digital circuit designed to process information, an analog circuit designed to process information, a state machine, and/or other mechanisms for electronically processing information. In order to provide the functionality attributed to controller 56 herein, controller 56 may execute one or more modules. The one or more modules may be implemented in software; hardware; firmware; some combination of software, hardware, and/or firmware; and/or otherwise implemented. Although controller 56 is shown in FIG. 1 as a single entity, this is for illustrative purposes only. In some implementations, controller 48 may include a plurality of processing units. These processing units may be physically located within the same device (e.g., sleep mask 10), or controller 56 may represent processing functionality of a plurality of devices operating in coordination.

In one embodiment, controller 56 controls first lighting module 16 and second lighting module 18 in accordance with a predetermined light therapy algorithm. The predetermined light therapy algorithm may dictate the timing, the intensity, and/or the wavelength of the radiation emitted by first lighting module 16 and second lighting module 18 toward the face of the subject on or about the eyes of the subject. In one embodiment, the predetermined light therapy algorithm is stored in electronic storage 52, and is provided to controller 56 for execution via control of first lighting module 16 and second lighting module 18. In some instances, one or more aspects of the predetermined light therapy algorithm may be adjusted or customized for the subject. Adjustments and/or customizations to the predetermined light therapy algorithm may be input to sleep mask 10 via user interface 54. In one embodiment, electronic storage 52 stores a plurality of different predetermined light therapy algorithms, and the subject (and/or a caregiver) select the predetermined light therapy algorithm that is appropriate for the subject via user interface 46.

As was mentioned above, in one embodiment, the predetermined light therapy algorithm may dictate the timing of the administration of radiation to the subject by sleep mask 10. As such, in this embodiment, controller 56 includes a clock. The clock may be capable of monitoring elapsed time from a given event and/or of monitoring the time of day. The subject (and/or a caregiver) may be enabled to correct the time of day generated by the clock of controller 56 via, for example, user interface 54.

In one embodiment, first lighting module 16 and/or second lighting module 18 are configured to emit electromagnetic radiation onto the closed eyelid of a subject when the subject is wearing sleep mask 10. In some embodiments, first lighting module 16 and second lighting module 18 are configured to emit electromagnetic radiation within a specific wavelength band. The wavelength band may be between about 490 nm and about 520 nm or between about 500 nm and about 510 nm so as to enable light therapy for modulation of circadian and related sleep cycle systems. Controller 56 is configured to control the timing and/or intensity of electromagnetic radiation emitted by first lighting module 16 and/or second lighting module 18.

The timing and/or intensity are controlled by controller 56 in accordance with a light therapy plan. In some embodiments, the light therapy plan may include a continuous light therapy plan. For example, in some embodiments, the light therapy plan delivered by mask 10 may include a bright light continuous therapy plan, wherein substantially continuous emission of light is emitted onto the closed eyelid of a subject at a substantially fixed intensity. In some embodiments, the light therapy plan may include a pulsed light therapy plan. For example, in some embodiments, the light therapy plan delivered by mask 10 may include bright light intermittent pulsed light therapy, wherein light in the wavelength band is pulsed upon a subject's eyelids. Other light therapy plans used by sleep mask 10 may include a brief cone-dominant pulsed light therapy.

FIG. 8 also illustrates that, in some embodiments, mask 10 may include one or more sensors 58 for sensing certain conditions at or near a subject's eyes such as, for example, light levels, eye movement, eyelid position, and/or other conditions. By way of example, one or more sensors 58 may include one or more photodiodes, CMOS (Complementary Metal-Oxide Semiconductor) detectors, photocells, CdS (Cadmium sulfide) cells, photoresistors, piezo-electric, mechanical strain sensors, magnetic search coils, and/or other sensors.

In some embodiments, lighting modules 16 and/or 18 may be driven or "actuated" by common circuits used to activate common light sources. In one embodiment, lighting modules 16 and/or 18 may utilize Light Emitting Diodes (LED) to provide the light described herein. LEDs may be activated by current regulated circuits, implemented in a digitally switched and/or analog current source type of circuit, which control the amount duty-cycle and regulation of current through the LEDs. Other light sources used for providing light described herein may also utilize this type or other common actuation elements required for their activation and control.

As illustrated in FIG. 6B, the level of light attenuation by eyelids of a patient may vary from patient to patient. As such, it may be useful in some embodiments of the invention to estimate the eyelid attenuation of a particular patient, prior to programming a light therapy plan into controller 56 or otherwise administering a light therapy plan to a subject. This may enable delivering a light therapy plan without using light in excess of the amount needed. For example, the power of the delivered light (i.e., irradiance) may be adjusted based on the estimated/measured attenuation of the eyelids (e.g., more attenuation=more intense light needed). In some instances, the eyelid attenuation of a given patient may be estimated by utilizing easily observable or discoverable characteristics of the patient (i.e., skin color, etc.). In some instances, eyelid attenuation may be estimated using other tests and equipment known in the art. In some instances, equipment for estimating a given patient's eyelid attenuation may interface with mask 10 or controller 56 via one or more of communication ports 60 so as to automatically enable controller 56 to determine the amount/strength of light for light therapy. In some instances, the radiation sources 44 of lighting modules 18 and/or 16 of mask 10 may be used as light sources for the estimation of eyelid attenuation of a given patient and may work in concert with additional equipment for providing this estimation.

In some embodiments, mask 10 may be configurable for use with open eye light therapy. For example, first and second lighting modules 16 and 18, as well as controller 56, power source 50, electronic storage 52 and/or other portions of mask 10 may be disconnected from shield 12 and may be attached or otherwise connected to a visor, lamp, light box, spectacle frames, goggles, and/or other open eye light therapy delivery device. Controller 56 may then be programmed to provide open eye light therapy using light having wavelengths closer to the "blue" end of the spectrum.

In some embodiments, mask 10 may include one or more of sensors 58 that are specifically configured to provide one or more of the following additional features: automated light level titration, sleep stage/state dependent operation, eye-opening detection, eye-movement detection, illuminance estimation, exposure time logging/limitation, safety warning, safety shut down, and/or other functions.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A sleep mask configured to provide light therapy to a subject, the sleep mask comprising:
   a shield configured to cover the eyes of a subject wearing the sleep mask such that the shield provides a barrier between ambient radiation and the eyes of the subject;
   a radiation source carried by the shield, the radiation source being configured to emit radiation onto a closed eyelid of the subject if the subject is wearing the sleep mask, wherein the radiation emitted by the radiation source is within a wavelength band between 490 nm and 520 nm; and
   a controller configured to:
      control emission of radiation by the radiation source to facilitate estimation of eyelid attenuation for the closed eyelid of the subject by the controller;
      estimate eyelid attenuation for the closed eyelid of the subject; and
      control emission of radiation by the radiation source based on the estimation of eyelid attenuation for the closed eyelid of the subject according to a light therapy plan that specifies an irradiance within the wavelength band that impacts a sleep cycle of the subject such that the radiation emitted by the radiation source within the wavelength band will have the irradiance specified by the light therapy plan after the radiation has been attenuated by the eyelid of the subject.

2. The sleep mask of claim 1, wherein the light therapy plan dictates continuous emission of the radiation by the radiation source at a fixed intensity.

3. The sleep mask of claim 1, wherein the light therapy plan dictates emission of the radiation by the radiation source in pulses.

4. The sleep mask of claim 1, wherein the wavelength band is between 500 nm and 510 nm.

5. A method of providing light therapy to a subject, the method comprising:

emitting electromagnetic radiation onto a closed eyelid of the subject, wherein the emitted radiation is within a wavelength band between 490 nm and 520 nm;

controlling emission of the electromagnetic radiation to facilitate estimation of eyelid attenuation for the closed eyelid of the subject;

estimating eyelid attenuation for the closed eyelid of the subject; and controlling emission of the electromagnetic radiation based on the estimation of eyelid attenuation for the closed eyelid of the subject according to a light therapy plan that specifies an irradiance within the wavelength band that impacts a sleep cycle of the subject such that the emitted radiation within the wavelength band will have the irradiance specified by the light therapy plan after the radiation has been attenuated by the eyelid of the subject.

6. The method of claim 5, wherein the light therapy plan dictates continuous emission of the radiation at a fixed intensity.

7. The method of claim 5, wherein the light therapy plan dictates emission of the radiation in pulses.

8. The method of claim 5, wherein the wavelength band is between 500 nm and 510 nm.

9. A system configured to provide light therapy to a subject, the system comprising:

means for emitting electromagnetic radiation onto a closed eyelid of the subject, wherein the emitted radiation is within a wavelength band between 490 nm and 520 nm;

means for controlling emission of the electromagnetic radiation to facilitate estimation of eyelid attenuation for the closed eyelid of the subject;

means for estimating eyelid attenuation for the closed eyelid of the subject; and means for controlling emission of the electromagnetic radiation based on the estimation of eyelid attenuation for the closed eyelid of the subject according to a light therapy plan that specifies an irradiance within the wavelength band that impacts a sleep cycle of the subject such that the emitted radiation within the wavelength band will have the irradiance specified by the light therapy plan after the radiation has been attenuated by the eyelid of the subject.

10. The system of claim 9, wherein the light therapy plan dictates continuous emission of the radiation by the means for emitting electromagnetic radiation at a fixed intensity.

11. The system of claim 9, wherein the light therapy plan dictates emission of the radiation by the means for emitting electromagnetic radiation in pulses.

12. The system of claim 9, wherein the wavelength band is between 500 nm and 510 nm.

\* \* \* \* \*